(12) United States Patent
Charlson et al.

(10) Patent No.: US 11,417,045 B2
(45) Date of Patent: Aug. 16, 2022

(54) DIALOG-BASED TESTING USING AVATAR VIRTUAL ASSISTANT

(71) Applicant: Battelle Memorial Institute, Columbus, OH (US)

(72) Inventors: David Mark Charlson, Columbus, OH (US); Richard Lawrence Shoaf, Westerville, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 253 days.

(21) Appl. No.: 16/841,769

(22) Filed: Apr. 7, 2020

(65) Prior Publication Data
US 2020/0320770 A1 Oct. 8, 2020

Related U.S. Application Data

(60) Provisional application No. 62/830,831, filed on Apr. 8, 2019.

(51) Int. Cl.
| | |
|---|---|
| *G06T 15/00* | (2011.01) |
| *G06F 3/01* | (2006.01) |
| *G10L 15/22* | (2006.01) |
| *G10L 25/63* | (2013.01) |
| *G06F 3/16* | (2006.01) |
| *G10L 15/08* | (2006.01) |
| *G06V 40/18* | (2022.01) |

(52) U.S. Cl.
CPC .......... *G06T 15/005* (2013.01); *G06F 3/012* (2013.01); *G06F 3/013* (2013.01); *G06F 3/167* (2013.01); *G06V 40/193* (2022.01); *G10L 15/08* (2013.01); *G10L 15/22* (2013.01); *G10L 25/63* (2013.01); *G10L 2015/088* (2013.01); *G10L 2015/223* (2013.01)

(58) Field of Classification Search
CPC ................................ G06F 3/013; G06F 3/167
See application file for complete search history.

(56) References Cited

U.S. PATENT DOCUMENTS

| | | | |
|---|---|---|---|
| 9,451,915 B1* | 9/2016 | Wong | G16H 40/63 |
| 2016/0062604 A1* | 3/2016 | Kraljic | G06F 3/0482 |
| | | | 715/771 |
| 2018/0307311 A1* | 10/2018 | Webb | G06F 3/013 |
| 2019/0026936 A1* | 1/2019 | Gorur Sheshagiri | |
| | | | G06T 19/006 |

(Continued)

*Primary Examiner* — Phi Hoang
(74) *Attorney, Agent, or Firm* — Fay Sharpe LLP (57) ABSTRACT

Dialog based testing is performed in conjunction with a three-dimensional (3D) virtual reality (VR) system including at least one loudspeaker, a microphone, and a 3D VR headset having a display for displaying 3D VR video and a gaze tracker integrated with the headset. The dialog based testing includes: rendering a 3D avatar via the display of the 3D VR headset; engaging in a dialog including causing the rendered 3D avatar to make utterances in accordance with the branching dialog script and receiving responses to the utterances from a test subject wearing the 3D VR headset including at least verbal responses received via the microphone and gaze activity recorded by the gaze tracker and traversing the branching dialog script including selecting branches of the branching dialog script based at least on the verbal responses received via the microphone; and grading the test subject based on the responses.

24 Claims, 3 Drawing Sheets

(56) References Cited

U.S. PATENT DOCUMENTS

2019/0171845 A1\* 6/2019 Dotan-Cohen ....... H04L 63/205
2020/0258047 A1\* 8/2020 Randall ................. G06N 3/006
2020/0297262 A1\* 9/2020 Chappell, III ..... H04N 21/8545

\* cited by examiner

DIALOG-BASED TESTING USING AVATAR VIRTUAL ASSISTANT

This application claims the benefit of provisional application No. 62/830,831 filed Apr. 8, 2019 and titled "DIALOG-BASED TESTING USING AVATAR VIRTUAL ASSISTANCE". Provisional application No. 62/830,831 filed Apr. 8, 2019 is incorporated herein by reference in its entirety.

BACKGROUND

The following relates to the dialog based subject credibility assessment arts, dialog based subject impairment testing arts, dialog based consumer preference evaluation arts, dialog based psychological assessment arts, and related dialog based testing arts.

Dialog based testing is used in a wide range of domains. In credibility assessment, the subject is engaged in a dialog with the intent of detecting any signs of untruthfulness, misrepresentation, or the like. Conventionally, this is done by direct person-to-subject dialog, for example an attorney questioning a witness, or a police officer questioning a suspect, or so forth, and may be relatively extemporaneous insofar as the questioner (attorney, police officer, et cetera) makes up the questions that are posed to the subject "on the fly". The questions are commonly a mixture of irrelevant questions intended to place the subject at ease and to provide a baseline of truthful responses, and pertinent questions (i.e., "test" questions) that are intended to elicit evidence of credibility. Usually, the questioner (e.g. attorney, police officer, et cetera) evaluates the credibility (i.e. truthfulness) of the subject based on subjective assessment of the content of the answers, time delays in answering, subjective assessment of "body language", and/or so forth. Such cues to dishonesty are expected to be exhibited (or exhibited more intensely) in responses to dishonest responses to test questions.

A polygraph test is a more sophisticated version of this, in which the subject is monitored by biometric sensors such as blood pressure, pulse, respiration, and skin conductivity during the questioning. In a polygraph test, the questions are usually scripted ahead of time, the person administering the polygraph test serves as the questioner, and the questioner/polygraph tester then assesses credibility of the subject after completion of the test based on a combination of the recorded biometric responses and subjective observations by the questioner/polygraph tester.

As another example, in subject impairment testing, the goal is to determine whether the subject is impaired by alcohol or drug intoxication. The well-known "Driving Under the Influence" test, commonly known as a DUI test, is one example. Here the dialog usually involves the test administrator instructing the test subject to perform various activities requiring coordination (e.g., walk in a straight line, speaking), and observing the success or failure of the test subject in these tasks. Intoxication is evidenced, for example, by inability to walk straight, slurring of speech, or so forth.

In dialog based consumer preference evaluations, the test administrator interacts with a test subject (or, in the interest of efficiency, a group of test subjects) who are presented with a product. The test administrator evaluates how well the product is received based on the objective responses (such as direct statements favoring or disfavoring the product) and based on subjective assessment of "body language".

In a dialog based psychological assessment, a clinician (e.g. psychologist, psychiatrist, mental health therapist, or so forth) poses questions to a patient or other person undergoing a psychiatric evaluation to assess characteristics such as level of depression, level of anxiety, suicidal tendency, whether the patient has a mental condition, and/or so forth. Again, the evaluations are usually based on a combination of the objective answers and on subjective observation of body language.

Disclosed herein are certain improvements suitably employed in one or more of these and/or other types of dialog based testing.

BRIEF SUMMARY

In accordance with some illustrative embodiments disclosed herein, a dialog based testing system comprises a three-dimensional (3D) virtual reality (VR) headset including a display for displaying 3D VR video and a gaze tracker integrated with the headset, at least one loudspeaker, a microphone, an electronic processor (operatively connected with the 3D VR headset, the at least one loudspeaker, the head movement sensor, and the microphone); and a non-transitory storage medium storing a branching dialog script and instructions readable and executable by the electronic processor to perform a dialog based testing method. The testing method includes: rendering a 3D avatar via the display of the 3D VR headset; engaging in a dialog including causing the rendered 3D avatar to make utterances in accordance with the branching dialog script and receiving responses to the utterances from a test subject wearing the 3D VR headset including at least verbal responses received via at least the microphone and gaze activity recorded by the gaze tracker and traversing the branching dialog script including selecting branches of the branching dialog script based on the verbal responses received via at least the microphone; assigning scores for the responses based at least on the gaze activity; and generating a report on the test subject based on the scores assigned for the responses.

In accordance with some illustrative embodiments disclosed herein, a non-transitory storage medium stores instructions readable and executable by a 3D VR system including an electronic processor, at least one loudspeaker, a microphone, and a 3D VR headset having a display for displaying 3D VR video integrated with the headset. The instructions are readable and executable by the 3D VR system to perform a dialog based testing method including: rendering a 3D avatar via the display of the 3D VR headset; engaging in a dialog including causing the rendered 3D avatar to make utterances in accordance with the branching dialog script, and receiving responses to the utterances from a test subject wearing the 3D VR headset including at least verbal responses received via the microphone, and traversing the branching dialog script including selecting branches of the branching dialog script based on at least the verbal responses received via the microphone; and generating a report on the test subject based on the responses.

In accordance with some illustrative embodiments disclosed herein, a dialog based testing method is performed in conjunction with a 3D VR system including at least one loudspeaker, a microphone, and a 3D VR headset having a display for displaying 3D VR video integrated with the headset. The dialog based testing method includes: rendering a 3D avatar via the display of the 3D VR headset; engaging in a dialog including causing the rendered 3D avatar to make utterances in accordance with the branching dialog script and receiving responses to the utterances from a test subject wearing the 3D VR headset including at least verbal responses received via the microphone, and traversing the branching dialog script including selecting branches of the branching dialog script based at least on the verbal responses received via the microphone; and grading the test subject based on the responses.

DETAILED DESCRIPTION

Existing dialog based testing approaches have certain disadvantages. They are subjective, at least to the extent that they rely upon subjective evaluation of "body language" by the test administrator. Such subjective evaluation is also inherently qualitative, even if some "rating scale" or other approach is employed in an effort to quantify the inherent subjectivity. The subjectivity and qualitative nature of the evaluation can be reduced, but not eliminated, by augmenting the subjective assessment of the test administrator with objective information such as biometric measurements.

Existing dialog based tests are also not well controlled, as there are numerous confounding factors that can impact the responses of the test subject. Some loss of control is inherent in the use of a human test administrator, as there will be variability in the way a particular test administrator engages in the dialog with the test subject. This variability is readily apparent in the case of extemporaneous dialog in which the test administrator makes up questions "on the fly". However, even if a prepared dialog script is accurately followed, there may be speech delays, variations in intonation, errant content delivery, and the like, along with variations in the "body language" of the test administrator. All these variations can impact the responses of the test subject. Indeed, interpersonal relationships are complex and difficult to predict, so that (for example) a certain test subject may simply dislike a certain test administrator (perhaps without even being able to articulate a reason), and this can impact the responses of the test subject.

Further confounding factors can arise due to the environment. Even if a dialog based test is performed in a designated testing room, there can be significant day-to-day variations in the content of the visual field observed by the test subject. The test administrator may be wearing different clothes on different days, or the scenery seen out of a window may change day to day or even moment to moment, a distracting mark of dirt may be left on a wall upon which the test subject fixates, or so forth. Also, a test subject who is placed in a room and engaged in dialog is likely to find this disconcerting, and this can impact the subject's responses. Baseline questions in a police interrogation or a polygraph test, for example, may not elicit the desired baseline responses since the test subject is agitated about being in (for example) a police interrogation room.

In embodiments disclosed herein, these and other disadvantages are remediated by way of performing dialog based testing using a three-dimensional (3D) virtual reality (VR) system that renders an avatar in 3D. The avatar performs the role of the test administrator who engages the test subject in the dialog. This approach for performing dialog based testing eliminates subjectivity of the dialog delivery on the part of the test administrator, as the avatar can be programmed to follow a prepared script exactly, with precisely the same speech delays, intonation, precise content delivery, and so forth being presented to each test subject. The avatar can be programmed to have exactly the same appearance for different test subjects; or, in other embodiments, an avatar specifically tailored to a particular test subject may be rendered.

Furthermore, existing 3D VR systems provide built-in sensors, typically including at least gaze tracking sensors and head motion sensors, and these are repurposed in embodiments disclosed herein to perform (previously subjective) assessments of responses of the subject. For example, gaze activity such as averted gaze is a common indicator of deception and hence are an effective indicator of lack of credibility—but rather than relying upon subjective and qualitative assessment of such gaze behavior as in existing dialog based testing, the 3D VR system based testing tracks the gaze using gaze trackers so as to provide a quantitative assessment of averted gaze. Furthermore, the gaze trackers of a 3D VR headset typically record images of the eyes, and these images can be evaluated to measure other biometrics such as pupil dilation which can be an indicator of intoxication. Advantageously, the gaze tracking sensors can detect microexpressions caused by conflicting voluntary and involuntary responses, which might be missed by a subjective evaluation of "body language".

A further advantage of the disclosed approaches is that they are immersive. The 3D VR headset completely blocks out the view of the external world so that the test subject sees only the computer-generated 3D avatar and the background that is programmed to be presented to the user. Again, sources of inter-subject test variation are thereby eliminated, as all test subjects see exactly the same background. The immersive experience can also present soothing scenery and the like that can reduce anxiety and enhance the quality of baseline responses.

The disclosed approaches employing a 3D avatar presented via a 3D VR system are also fully compatible with the use of other biosensors (beyond the gaze tracker and head movement sensors of the 3D VR system). Hence, a 3D VR driven polygraph test is contemplated, in which subjectivity inherent in the human test administrator is eliminated, being replaced by fully objective metric such as quantitatively measured gaze activity, pupil dilation, and head movement metrics.

Figure 1:
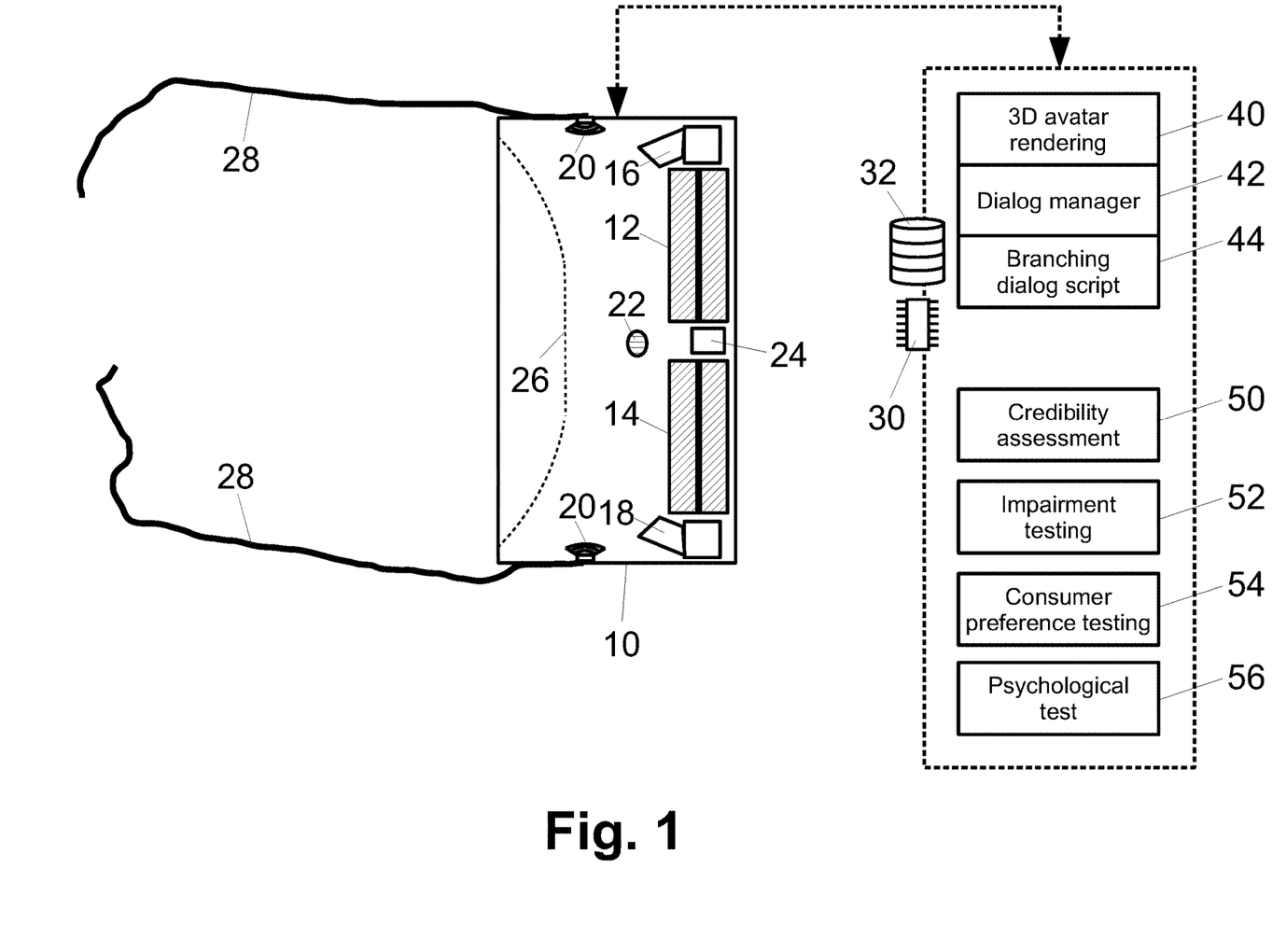
FIG. 1 diagrammatically illustrates a dialog based testing system for performing dialog based testing of a subject.

With reference to FIG. 1, an illustrative dialog based testing system includes a three-dimensional (3D) virtual reality (VR) headset 10 including a display 12, 14 for displaying a 3D VR video and a gaze tracker 16, 18 integrated with the headset 10. The illustrative display includes a left display 12 aligned to be viewed by the left eye of a test subject wearing the 3D VR headset 10 and a right display 14 aligned to be viewed by the right eye of the test subject wearing the 3D VR headset 10. Similarly, the gaze tracker includes a left-eye gaze tracker 16 aligned to image the left eye of the of test subject wearing the 3D VR headset 10 and a right gaze tracker 18 aligned to image the right eye of the of test subject wearing the 3D VR headset 10. The 3D VR headset 10 optionally includes additional components, such as one or more loudspeakers 20 (which may be optionally implemented as earphones; alternatively, the sound may be provided by an external surround sound system or the like rather than being integrated with the headset 10), a microphone 22, an accelerometer or other head motion sensor 24 mounted on the headset 10 (alternatively, an external motion sensor such as a video camera based motion sensor may be employed); and/or so forth. The illustrative 3D VR headset 10 includes a forehead rest 26 and straps 28 for securing the 3D VR headset 10 to the head of the test subject with the left and right eyes aligned with the left and right displays 12, 14 respectively.

An electronic processor 30 is, for example, a microprocessor and/or microcontroller and/or graphical processing unit (GPU), and may include or be connected with ancillary components such as random access memory (RAM), external circuitry providing wired and/or wireless connection with the various electronic components 12, 14, 16, 18, 20, 22, 24 of the 3D VR headset 10 and/or so forth. The electronic processor 30 is operatively connected with a non-transitory storage medium 32 to read and execute instructions stored on the non-transitory storage medium 32 to operate the 3D VR headset 10 to perform a dialog based testing method as disclosed herein. The electronic processor 30 may be integrated with (e.g. disposed in) the headset 10 and/or disposed in (or formed by) a computer or electronic VR console (not shown), or some combination thereof (e.g. a main processor disposed in the console and an on-board processor disposed in the headset 10). The non-transitory storage medium 32 may, by way of non-limiting illustrative example, include one or more of: a solid state drive (SSD), flash memory, or other electronic storage medium; a hard disk drive or other magnetic storage medium; an optical disk or other optical storage medium; various combinations thereof; and/or so forth.

The 3D VR headset 10 and electronic processor 30 may comprise a commercial virtual reality system programmed to perform dialog based testing as disclosed herein, such as an Oculus Rift system, a Sony Playstation VR system, or so forth. As disclosed herein, the 3D VR system is programmed to implement the dialog based testing using a 3D avatar rendering module 40 and a dialog manager 42 implementing a branching dialog script 44. These components may be employed to implement various types of dialog based testing depending on the choice of the branching dialog script 44 and scripted dialog (and optionally also scripted actions) of the 3D avatar and optionally also scripted 3D VR video content presented as part of the script. In general, the dialog based testing method includes: rendering a 3D avatar via the display 12, 14 of the 3D VR headset 10; engaging in a dialog including causing the rendered 3D avatar to make utterances in accordance with the branching dialog script 44 and receiving responses to the utterances from a test subject wearing the 3D VR headset 10 including at least verbal responses received via at least the microphone 22 and gaze activity recorded by the gaze tracker 16, 18 and traversing the branching dialog script 44 including selecting branches of the branching dialog script based on the verbal responses received via at least the microphone; assigning scores for the responses based at least on the gaze activity; and generating a report on the test subject based on the scores assigned for the responses.

For example, a dialog based credibility assessment test 50 can be implemented by the dialog based testing system of FIG. 1. In this type of testing, the scores for the responses may include assigning credibility scores for the responses based on the gaze activity including whether a response to an utterance comprising a test question includes an averted gaze (insofar as gaze aversion is a known indicator of a lack of credibility). The credibility scores may be further based on expected content of verbal responses defined in the branching dialog script. For example, the script may include questions for which the correct answer is known (and furthermore it is known that the test subject knows the correct answer) and hence these questions provide a baseline for assessing credibility. In some implementations of the credibility assessment test 50, the head motion sensor 24 is also used, and the credibility scores for at least some responses are assigned further based on head motion measured by the head motion sensor in response to an utterance comprising a test question. For example, a slight movement of the head away from eye contact with the questioner (i.e. the rendered 3D avatar) may indicate a lack of truthfulness. In some implementations of the credibility assessment test 50, the response delay time in responding to the question is also used, and the credibility scores for at least some responses are assigned further based on the response delay time prior to receiving the response to the test question. This is premised by the expectation that a slight delay in responding can be indicative of a lack of truthfulness.

As another example, a dialog based impairment test 52 can be implemented by the dialog based testing system of FIG. 1. In this case, the assigning of scores for the responses may include assigning coordination scores for the responses based on the gaze activity including whether the gaze activity indicates a lack of coordination (which is taken as evidence of impairment due to alcohol or drug intoxication). For example, in one possible implementation of the impairment test 52, the dialog based impairment testing method includes rendering an object or a hand of the rendered 3D avatar via the display 12, 14 of the 3D VR headset 10 and moving the rendered object or hand in 3D space while engaging in the dialog. The branching dialog script includes an instructional utterance made by the rendered 3D avatar while moving the hand or object in 3D space instructing the test subject to visually follow the moving object hand or object. The assigning of scores for the responses includes assigning a coordination score for the instructional utterance based on accuracy of the gaze activity in following the hand or object after the instructional utterance (where poor coordination in following the hand or object with the gaze is indicative of impairment). In another possible dialog script (or script portion), the branching dialog script includes a speech test utterance made by the rendered 3D avatar instructing the test subject to utter a test word or phrase, and the assigning of scores for the responses includes assigning a coordination score for the speech test utterance based on (i) fidelity of the verbal response to the speech test utterance with the test word or phrase (misspeaking the phrase being taken as possible indication of impairment of short-term memory) and/or (ii) a measure of slurring of the verbal response to the speech test utterance (excessive slurring being an indication of impairment). Optionally, the head motion sensor 24 may be utilized, and the coordination scores for the responses are thereby assigned further based on whether head motion measured by the head motion sensor indicates a lack of coordination.

As another example, a dialog based consumer preference test 54 can be implemented by the dialog based testing system of FIG. 1. In this case, the dialog based consumer preference testing method includes rendering a product (that is, the product for which consumer preference is to be assessed) via the display 12, 14 of the 3D VR headset 10, and the assigning of scores for the responses includes assigning a consumer preference score based on a measure of gaze focus on the rendered product. A strong gaze focus on the product may indicate a desire for the product (i.e. strong positive preference) whereas a weak gaze focus, such as not looking at the product or glancing away from it, may indicate a low or negative preference for the product. In a variant of this, the product under test may be shown along with other similar products by the same vendor or by competitor(s), and the ratio of gaze focus amongst the various products can be used to assess relative preferences. Optionally, the head motion sensor 24 may also be used, and the consumer preference scores are suitably assigned further based on whether head motion measured by the head motion sensor 24 includes a back-and-forth head shaking motion (this being a common nonverbal cue of disapproval). Similarly, an up-and-down head shaking motion may be a cue of approval.

As yet another non-limiting illustrative example, a dialog based psychological test 56, such as a psychiatric evaluation for depression, suicidal tendency, or so forth, can be implemented by the dialog based testing system of FIG. 1. Again, the gaze tracker 16, 18 and/or head motion sensor 24 may be used to detect nonverbal cues that, based on clinical studies or the like, are believed to be indicative of the psychological characteristic under test. In addition, verbal cues such as keywords or phrases may be detected to indicate psychological issues.

The gaze tracker 16, 18 typically operates by acquiring video of the eyes of the test subject, i.e. the left gaze tracker 16 images the left eye while the right gaze tracker 18 images the right eye. Gaze tracking is based on the direction of the pupils, while depth focus can be adduced from the slight difference in gaze direction between the two eyes. In some embodiments, the gaze tracker 16, 18 gaze tracker also measures pupil dilation, as this information is readily extracted from video of the pupil. The received responses to the utterances by the 3D avatar during the dialog based testing may then further include pupil dilation measurements by the gaze tracker 16, 18, and the scores for the responses are then optionally assigned further based on the pupil dilation measurements by the gaze tracker. For example, pupil dilation can be an indicator of intoxication.

The dialog based testing method is intended to generate a result which may, or may not, be intended to be conveyed to the test subject. For example, in credibility testing 50, the test subject may not be told of the result (or may not be immediately told of the result). Likewise in consumer preference testing 54 it is usually the case that the test result is not conveyed to the test subjects. Hence, in some embodiments, the dialog based testing method does not include presenting the report to the test subject via the 3D VR headset 10.

The disclosed dialog based testing system employs the 3D VR headset 10 presenting a rendering of a 3D avatar who serves as a virtual test administrator (e.g. virtual questioner) who presents dialog in accordance with the branching dialog script 44. The dialog manager 42 provides for traversing the script 44.

Figure 2:
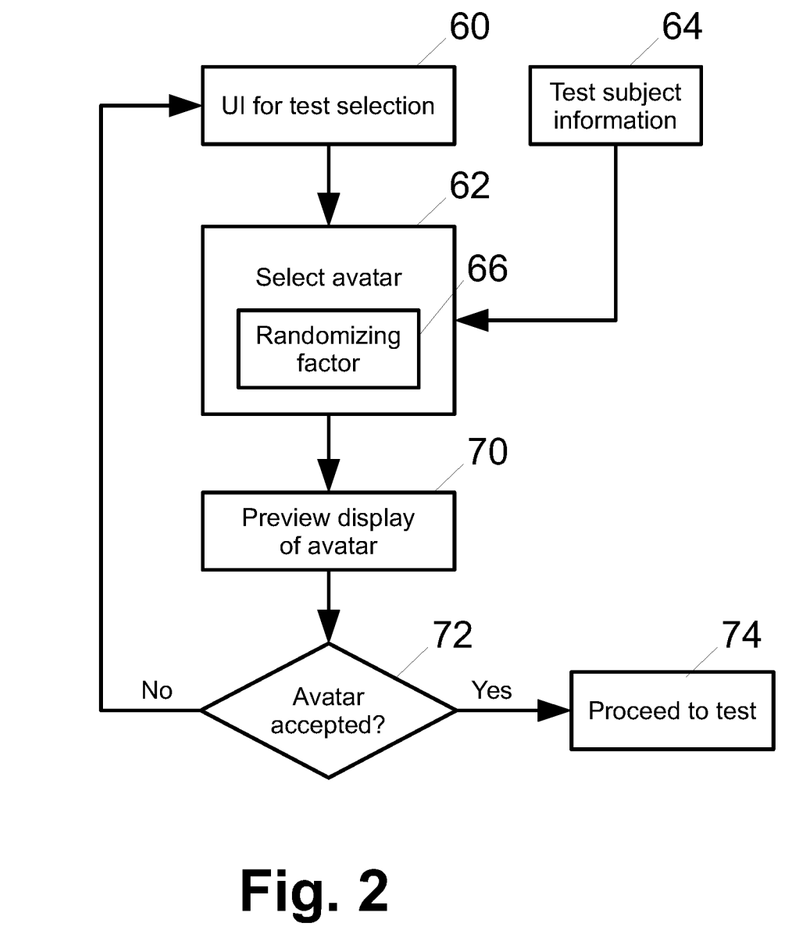
FIG. 2 diagrammatically shows an avatar selection method suitably performed by the system of FIG. 1.

With reference to FIG. 2, in some embodiments a user interface (UI) 60 is provided via which a human test administrator sets up the dialog based test including selecting 62 the 3D avatar. (this UI 60 is typically a computer with a display and keyboard/mouse/other user input device(s), not shown, rather than employing the 3D VR headset 10). This may be done in various ways, for example selecting the 3D avatar from a set of preprogrammed avatars. Information 64 on the test subject may be leveraged in this selection. For example, it may be desirable to choose a 3D avatar of the same gender and/or ethnicity as the test subject in order to place the test subject at ease (or, conversely, the gender and/or ethnicity may be selected to be different from that of the test subject if this arrangement is believed to be advantageous, e.g. if testing credibility of a person suspected of committing a hate crime). Optionally, a randomizing factor 66 may be incorporated into the 3D avatar selection. This may include randomizing the selection of the 3D avatar from a set of preprogrammed avatars, or randomizing selected characteristics of a given preprogrammed 3D avatar, or both. Such randomization may, for example, be useful to generate a uniform distribution of virtual test administrators for performing a series of tests on a set of subjects in the context of a clinical psychology study. The rendered 3D avatar may optionally be displayed 70 to the human test administrator for approval before being employed in the test. (This will usually be on the two-dimensional screen of the setup computer, not shown, rather than via the 3D VR headset 10). At decision 72, the 3D avatar is selected, in which case the process flow proceeds to test 74; or, if the avatar is not approved then process flow goes back to the UI 60 to update or reselect the 3D avatar.

Figure 3:
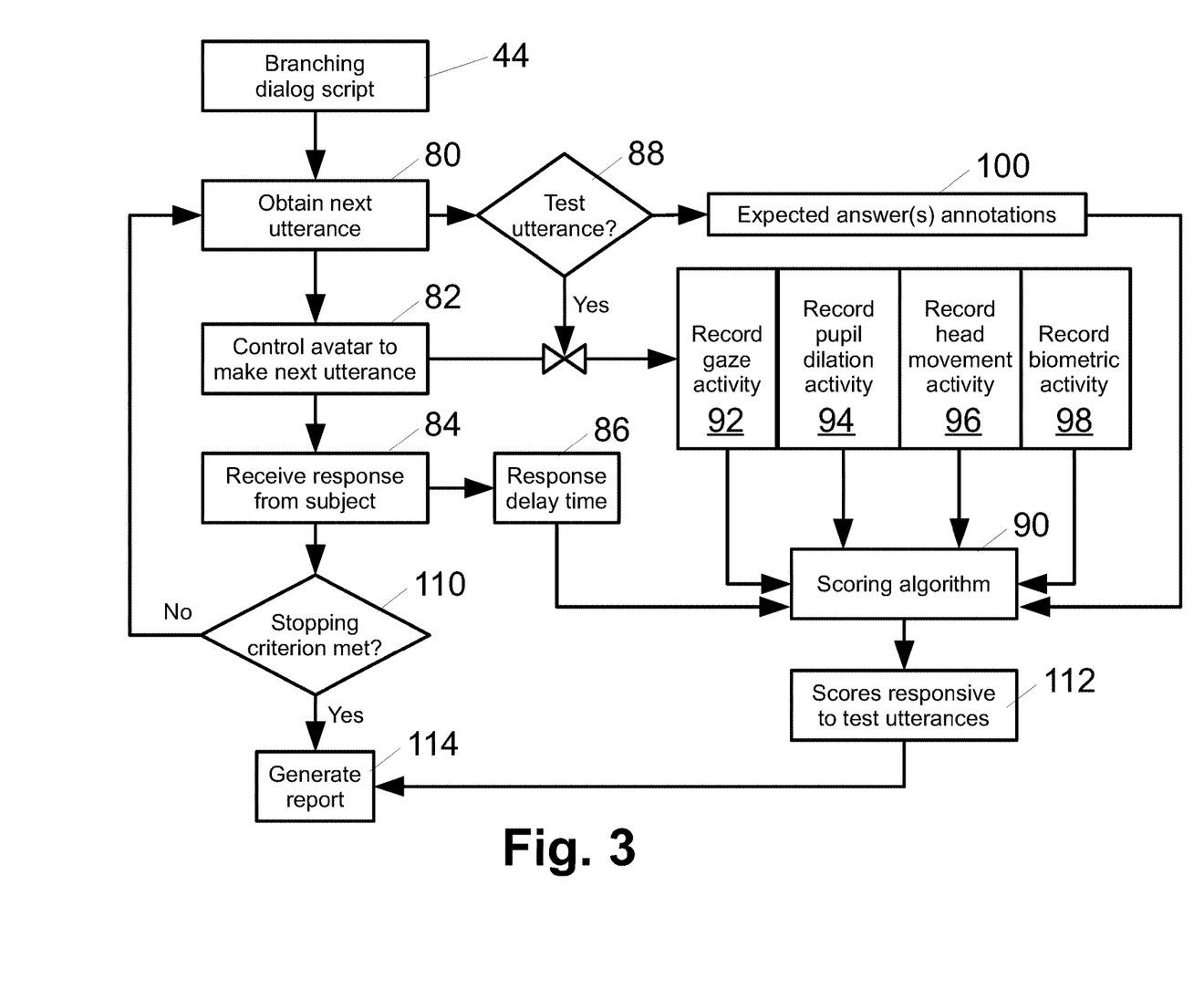
FIG. 3 diagrammatically shows a dialog based testing method suitably performed by the system of FIG. 1.

With reference now to FIG. 3, an illustrative example of traversing the branching dialog script 44 is shown. The dialog manager 42 (see FIG. 1) provides for traversing the script 44. At a given point in the script execution, the next utterance to be uttered is selected 80. This is the next utterance to be executed by the virtual test administrator or questioner (who is the rendered 3D avatar in the disclosed approach). At operation 82, the electronic processor 30 controls the VR system to control the 3D avatar to make the selected next utterance. An advantage of the disclosed system is that the script 44 may define the utterance in much greater detail than merely a natural language text of the utterance. The selected utterance 80 may also include (by way of non-limiting illustrative example) nonverbal cues that the 3D avatar is programmed to perform as part of the utterance (for example, a particular facial expression, shoulder shrug, et cetera), detailed cadence, delays between words, or other aspects of the verbal delivery of the utterance by the 3D avatar, additional 3D VR renderings associated with the utterance (for example, a moving object or hand accompanying an instruction to follow the object/hand with the gaze during an impairment test), and/or so forth. The various sensors (e.g. gaze tracker 16, 18, microphone 22, head tracker 24, and/or so forth) then monitor the test subject to receive the response 84. The response includes the natural language textual content recorded by the microphone 22 and suitably converted to natural language text by speech recognition software). However, as with executing the utterance, the response received at 84 may include more than the text itself. The response may include other information such as gaze activity recorded by the gaze tracker 16, 18, head movements recorded by the head motion sensor 24, extracted features related to the cadence of the verbal response, a response time delay 86, and/or so forth.

The script 44 also indicates what is to be done with the response 84 to the utterance selected at 80. For example, in some dialog based test designs, the responses to some utterances are not graded as part of the test. For example, some utterances may be introductory pleasantries intended to place the test subject at ease. Some utterances may be utterances intended to orient the test subject (e.g. explaining the upcoming test process), or transitional utterances intended to guide the test subject from one phase of the test to the next phase. These types of utterances are not graded as part of the dialog based test. On the other hand, the test also includes utterances, referred to herein as test utterances, which are graded as part of the test. These test utterances may be directly related to the subject matter being tested (e.g., asking about a product being presented as part of a consumer preference test 54, or a question directly pertinent to a matter on which the test subject's veracity is being tested as part of a credibility test 50, or so forth), or the test utterances may be baseline test utterances intended to establish the baseline response of the test subject. At decision 88 of FIG. 3, it is determined whether the utterance obtained at 80 is a test utterance. (In a suitable approach, each utterance of the branching test dialog 44 is labeled as to whether it is a test utterance, and this label is read to make the decision 88). If the utterance is a test utterance, then a scoring algorithm 90 is applied to score the response 84. The inputs to the scoring algorithm may include (by way of non-limiting example) gaze activity 92, pupil dilation measurements 94, head movement activity 96, biometric activity 98 if available (for example, if a credibility test 50 is being implemented as a polygraph test, then the test subject is suitably monitored by biometric sensors such as blood pressure, pulse, respiration, and skin conductivity during the traversal of the branching dialog script 44), and/or so forth. Furthermore, if the utterance selected at 80 is annotated in the script 44 with an expected answer (e.g. the true answer, or a typical answer given the context, or a set of expected answers such as "yes" or "no" in response to an utterance which is a yes-or-no question) then the scoring algorithm 90 compares the textual content of the spoken response with an expected answer or set of expected answers 100 taken from the script 44 in assigning the score. As previously mentioned, other information such as the response time delay 86 and/or features quantifying the cadence, slurring, or other aspects of the speech, may be used by the scoring algorithm 90. It will be appreciated that the scoring algorithm 90 may be different for different test utterances of the branching dialog script 44, and are suitably designed by a test designer (e.g. a polygraph expert, psychologist, consumer testing expert, or so forth).

With continuing reference to FIG. 3, the scoring process 88, 90 and associated inputs 86, 92, 94, 96, 98, 100 are recorded in real time or retrieved from the script 44 (an essentially instantaneous action), so that the scoring process for test utterances introduces no delay. Hence, immediately upon receiving the response 84, the dialog manager 42 determines at 110 whether a stopping criterion has been met (e.g., the concluding pleasantry utterances having been executed). If not, then process flow returns to 80 to select the next utterance from the branching dialog script 44. This may entail branching along the script based on the content of the received response 84. The branch path selection is usually determined based on the textual content of the response (as extracted by voice recognition) but may additionally or alternatively be determined based on nonverbal information. For example, if the gaze tracking 92 suggests the response was untruthful then this may cause the dialog manager 42 to select a branch following up on the suspected untruthfulness of the response. As with the scoring algorithm 90, the branching dialog script 44 including the decision criteria at branch points is suitably designed by a test designer (e.g. a polygraph expert, psychologist, consumer testing expert, or so forth).

When the dialog manager determines at 110 that the dialog is complete, then the scores 112 to all executed test questions are used in report generation 114. As with the script 44 and the scoring algorithm 90, the report generation 114 is suitably designed by the test designer (e.g. a polygraph expert, psychologist, consumer testing expert, or so forth). It should be noted that the scores 112 may not include scores for all possible test questions in the script 44, since branches of the branching dialog script 44 which are not followed may include test questions that were never traversed. The report may be strictly quantitative, e.g. listing scores for the various responses, or may be converted to natural language format using a suitable reporting template.

In embodiments disclosed herein, a computer generated avatar is hosted in a virtual reality world for conversing with humans in a realistic environment. This includes real-time lip synchronization, text-to-speech, speech recognition, multiple languages, multiple ethnicities, animated facial expressions and emotions. Data are recorded using cameras, microphones and biometric sensors for analyses such as credibility assessments or assessment of physical/mental impairment. The disclosed approaches establish a conversational interface to a computer system. It provides a mechanism to engage the user in a natural activity while discreetly or overtly monitoring biometric data, such as pupil tracking data, for credibility assessment. This can be used for information dissemination, user evaluation, mental health therapy and assistance, or so forth. The avatar virtual assistant integrates a computer-generated avatar into a virtual reality or augmented reality environment. Coupled with integration of eye-tracking into a virtual reality environment, it provides the ability to discreetly monitor and record gaze-tracking and pupilometric data without the user's knowledge. By setting up natural communications in a virtual environment, a user can have a more intuitive interface with a complex system. It provides the ability to interview subjects, evaluate credibility, or assist with individuals for mental health in a comfortable environment. Some features that may be incorporated include one or more of the following: a computer-generated avatar with the likeness of a human; customizable avatar for gender and multiple ethnicities; real-time lip synchronization; configurable animations and emotions for enhanced realism; multiple language support for text-to-speech and speech recognition; foreign language instrumentation performed in English without knowledge of the target language; precise collection and storage of user response and timing data for later analysis; audio and video data recorded for later analysis; monitoring and recording of biometric data including heart rate, blood oxygen saturation, eye tracking, and thermal images; natural language interaction using modern service-based speech recognition and artificial intelligence; and scripted, repeatable interviews for consistency between multiple users.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A dialog based testing system comprising:
   a three-dimensional (3D) virtual reality (VR) headset including a display for displaying 3D VR video and a gaze tracker integrated with the headset;
   at least one loudspeaker;
   a microphone;
   an electronic processor operatively connected with the 3D VR headset, the at least one loudspeaker, the head movement sensor, and the microphone; and
   a non-transitory storage medium storing a branching dialog script and instructions readable and executable by the electronic processor to perform a dialog based testing method including:
   rendering a 3D avatar via the display of the 3D VR headset;

engaging in a dialog including causing the rendered 3D avatar to make utterances in accordance with the branching dialog script and receiving responses to the utterances from a test subject wearing the 3D VR headset including at least verbal responses received via at least the microphone and gaze activity recorded by the gaze tracker and traversing the branching dialog script including selecting branches of the branching dialog script based on the verbal responses received via at least the microphone;

assigning scores for the responses based at least on the gaze activity; and generating a report on the test subject based on the scores assigned for the responses.

2. The dialog based testing system of claim 1 wherein the dialog based testing method is a dialog based credibility testing method and the assigning of scores for the responses includes assigning credibility scores for the responses based on the gaze activity including whether a response to an utterance comprising a test question includes an averted gaze.

3. The dialog based testing system of claim 2 wherein the credibility scores are further based on expected content of verbal responses defined in the branching dialog script and/or a response delay time prior to receiving the response to the test question.

4. The dialog based testing system of claim 2 further comprising:

a head motion sensor, the credibility scores for the responses being assigned further based on head motion measured by the head motion sensor in response to an utterance comprising a test question.

5. The dialog based testing system of claim 1 wherein the dialog based testing method is a dialog based impairment testing method and the assigning of scores for the responses includes assigning coordination scores for the responses based on the gaze activity including whether the gaze activity indicates a lack of coordination.

6. The dialog based testing system of claim 5 wherein:

the dialog based impairment testing method includes rendering an object or a hand of the rendered 3D avatar via the display of the 3D VR headset and moving the rendered object or hand in 3D space while engaging in the dialog;

the branching dialog script includes an instructional utterance made by the rendered 3D avatar while moving the hand or object in 3D space instructing the test subject to visually follow the moving object hand or object; and the assigning of scores for the responses includes assigning a coordination score for the instructional utterance based on accuracy of the gaze activity in following the hand or object after the instructional utterance.

7. The dialog based testing system of claim 5 wherein:

the branching dialog script includes a speech test utterance made by the rendered 3D avatar instructing the test subject to utter a test word or phrase; and the assigning of scores for the responses includes assigning a coordination score for the speech test utterance based on a combination of (i) fidelity of the verbal response to the speech test utterance with the test word or phrase and (ii) a measure of slurring of the verbal response to the speech test utterance.

8. The dialog based testing system of claim 5 further comprising:

a head motion sensor, the coordination scores for the responses being assigned further based on whether head motion measured by the head motion sensor indicates a lack of coordination.

9. The dialog based testing system of claim 1 wherein the dialog based testing method is a dialog based consumer preference testing method and wherein:

the dialog based consumer preference testing method includes rendering a product via the display of the 3D VR headset;

the assigning of scores for the responses includes assigning a consumer preference score based on a measure of gaze focus on the rendered product.

10. The dialog based testing system of claim 9 further comprising:

a head motion sensor, the consumer preference scores being assigned further based on whether head motion measured by the head motion sensor includes a back-and-forth head shaking motion and/or an up-and-down head shaking motion.

11. The dialog based testing system of claim 1 wherein the dialog based testing method is a dialog based psychological testing method and the assigning of scores is based at least on verbal cues including keywords or phrases indicative of a psychological issue.

12. The dialog based testing system of claim 1 wherein the gaze tracker also measures pupil dilation, and the received responses to the utterances further include pupil dilation measurements by the gaze tracker, and the scores for the responses are assigned further based on the pupil dilation measurements by the gaze tracker.

13. The dialog based testing system of claim 1 wherein the dialog based testing method does not include presenting the report to the test subject via the 3D VR headset.

14. A non-transitory storage medium storing instructions readable and executable by a three-dimensional (3D) virtual reality (VR) system including an electronic processor, at least one loudspeaker, a microphone, a 3D VR headset having a display for displaying 3D VR video integrated with the headset, and a gaze tracker integrated with the headset, the instructions being readable and executable by the 3D VR system to perform a dialog based testing method including:

rendering a 3D avatar via the display of the 3D VR headset;

engaging in a dialog including causing the rendered 3D avatar to make utterances in accordance with the branching dialog script, and receiving responses to the utterances from a test subject wearing the 3D VR headset including at least verbal responses received via the microphone and gaze activity recorded by the gaze tracker, and traversing the branching dialog script including selecting branches of the branching dialog script based at least on the verbal responses received via the microphone;

assigning scores for the responses based at least on the gaze activity; and generating a report on the test subject based on the scores assigned for the responses.

15. A dialog based testing method performed in conjunction with a three-dimensional (3D) virtual reality (VR) system including at least one loudspeaker, a microphone, a 3D VR headset having a display for displaying 3D VR video integrated with the headset, and a gaze tracker integrated with the headset, the dialog based testing method including:

rendering a 3D avatar via the display of the 3D VR headset;

engaging in a dialog including causing the rendered 3D avatar to make utterances in accordance with the branching dialog script, and receiving responses to the utterances from a test subject wearing the 3D VR headset including at least verbal responses received via the microphone and gaze activity recorded by the gaze tracker, and traversing the branching dialog script including selecting branches of the branching dialog script based at least on the verbal responses received via the microphone; and assigning scores for the test subject based at least on the gaze activity.

16. The dialog based testing method of claim 15 wherein the dialog based testing method is a dialog based credibility testing method and the scores are assigned based on detection of averted gaze in the gaze activity.

17. The dialog based testing method of claim 15 wherein the dialog based testing method is a dialog based impairment testing method and the scores are assigned based on a coordination assessment of the gaze activity.

18. The dialog based testing method of claim 17 wherein:
the dialog based impairment testing method includes rendering an object or a hand of the rendered 3D avatar via the display of the 3D VR headset and moving the rendered object or hand in 3D space while engaging in the dialog;
the branching dialog script includes an instructional utterance made by the rendered 3D avatar while moving the hand or object in 3D space instructing the test subject to visually follow the moving object hand or object; and
the scores are assigned based at least in part on a coordination assessment of the gaze activity in following the hand or object after the instructional utterance.

19. The dialog based testing method of claim 17 wherein:
the branching dialog script includes a speech test utterance made by the rendered 3D avatar instructing the test subject to utter a test word or phrase; and
the scores are assigned based at least in part on a measure of slurring of the verbal response to the speech test utterance.

20. The dialog based testing method of claim 15 wherein the dialog based testing method is a dialog based consumer preference testing method further including rendering a product via the display of the 3D VR headset and the scores are assigned based at least in part on gaze focus on the rendered product.

21. The dialog based testing method of claim 20 wherein the 3D VR system further includes a head motion sensor and the scores are assigned further based on whether a back-and-forth head shaking motion and/or an up-and-down head shaking motion is measured by the head motion sensor.

22. A dialog based testing method performed in conjunction with a three-dimensional (3D) virtual reality (VR) system including at least one loudspeaker, a microphone, and a 3D VR headset having a display for displaying 3D VR video integrated with the headset, the dialog based testing method including:

rendering a 3D avatar via the display of the 3D VR headset;

engaging in a dialog including causing the rendered 3D avatar to make utterances in accordance with the branching dialog script, and receiving responses to the utterances from a test subject wearing the 3D VR headset including at least verbal responses received via the microphone, and traversing the branching dialog script including selecting branches of the branching dialog script based at least on the verbal responses received via the microphone; and assigning scores for the test subject based on the responses;

wherein the dialog based testing method is a dialog based psychological testing method and the scores are assigned based at least on verbal cues including keywords or phrases indicative of a psychological issue.

23. The dialog based testing method of claim 15 wherein the gaze tracker also measures pupil dilation, and the received responses to the utterances further include pupil dilation measurements by the gaze tracker, and the scores are assigned further based on the pupil dilation measurements by the gaze tracker.

24. The dialog based testing method of claim 15 wherein the dialog based testing method does not include presenting the scores to the test subject via the 3D VR headset.

* * * * *